(12) United States Patent
Bellian et al.

(10) Patent No.: US 9,140,643 B2
(45) Date of Patent: Sep. 22, 2015

(54) SYSTEM AND METHOD FOR INTERROGATION OF TARGET MATERIAL IN SITU

(75) Inventors: Jerome Anthony Bellian, Danville, CA (US); Christopher Michael Tolleson, Austin, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 474 days.

(21) Appl. No.: 13/444,116

(22) Filed: Apr. 11, 2012

(65) Prior Publication Data

US 2013/0271752 A1   Oct. 17, 2013

(51) Int. Cl.
*G01J 3/28* (2006.01)
*G01N 21/27* (2006.01)
*G01N 21/55* (2014.01)
*G01J 3/26* (2006.01)
*G01S 17/89* (2006.01)
*G01S 7/48* (2006.01)
*G01V 8/02* (2006.01)
*G01J 3/02* (2006.01)
*G01N 21/31* (2006.01)

(52) U.S. Cl.
CPC ............... *G01N 21/27* (2013.01); *G01J 3/027* (2013.01); *G01J 3/26* (2013.01); *G01N 21/314* (2013.01); *G01N 21/55* (2013.01); *G01S 7/4802* (2013.01); *G01S 17/89* (2013.01); *G01V 8/02* (2013.01)

(58) Field of Classification Search
CPC .................................. G01J 3/26; G01S 17/89
USPC ......... 356/445, 300, 72–73, 451, 456; 385/12
See application file for complete search history.

(56) References Cited

U.S. PATENT DOCUMENTS

| 5,450,125 | A | | 9/1995 | Ulich et al. | |
| 5,838,437 | A | * | 11/1998 | Miller et al. | 356/478 |
| 6,449,047 | B1 | * | 9/2002 | Bao et al. | 356/478 |

(Continued)

FOREIGN PATENT DOCUMENTS

| EP | 1569007 A2 | 8/2005 |
| EP | 1970684 A1 | 9/2008 |

(Continued)

OTHER PUBLICATIONS

Adams, E. W., Bellian, J.A., Reyes, R., 2009, Digital Outcrop Models Reduce Uncertainty and Improve Reservoir Characterization, World Oil, September, p. 46-49.

(Continued)

*Primary Examiner* — Kara E Geisel
(74) *Attorney, Agent, or Firm* — Albert K. Shung

(57) ABSTRACT

A system for remotely sensing a target material in situ include a broad-band laser source, at least one tunable filter coupled to the source laser for generating a swept-frequency signal an optical device for splitting the swept-frequency signal into a first illumination signal and second illumination signal, a first optical path for directing the first illumination signal unto the target material and receiving a reflected signal from the target material, a second optical path for receiving the second illumination signal and generating a spectral reference signal, and a controller coupled to the first optical path and the second optical path for adjusting the frequency and spatial resolution of the laser source based at least in part on a comparison of the spectral reference signal and the reflected signal.

17 Claims, 3 Drawing Sheets

(56) References Cited

U.S. PATENT DOCUMENTS

| | | | |
|---|---|---|---|
| 6,509,566 | B1 | 1/2003 | Wamsley et al. |
| 6,608,677 | B1 | 8/2003 | Ray et al. |
| 6,967,322 | B2 | 11/2005 | Jones et al. |
| 6,995,846 | B2 | 2/2006 | Kalayeh et al. |
| 7,009,170 | B2 | 3/2006 | Dobbs et al. |
| 7,060,967 | B2 * | 6/2006 | Thingbo et al. .......... 250/227.18 |
| 7,379,180 | B2 | 5/2008 | Vannuffelen et al. |
| 7,474,685 | B2 | 1/2009 | Kalayeh |
| 7,573,021 | B2 * | 8/2009 | Haber et al. ............. 250/227.14 |
| 7,601,950 | B2 | 10/2009 | Kischkat et al. |
| 7,639,347 | B2 | 12/2009 | Eaton |
| 7,859,654 | B2 | 12/2010 | Hartog |
| 2007/0280703 | A1 * | 12/2007 | Taverner et al. .............. 398/195 |
| 2008/0170218 | A1 | 7/2008 | Dantus et al. |
| 2009/0256412 | A1 | 10/2009 | Nieto et al. |

FOREIGN PATENT DOCUMENTS

| | | |
|---|---|---|
| WO | 2004003506 | 1/2004 |
| WO | 2011016892 | 7/2008 |

OTHER PUBLICATIONS

Bellian, J.A., Kerans, C., and Jennette, D.C., 2005, Digital outcrop models: applications of terrestrial scanning lidar technology in stratigraphic modeling: Journal of Sedimentary Research, v. 75, No. 2, p. 166-176.

Burton, Darrin, Dunlap, Dallas, Wood, Leslie, Flaig, Peter, 2011, Lidar intensity as a remote sensor of rock properties, Journal of Sedimentary Research, May 2011, vol. 81, Issue 5, pp. 339-347.

Franceschi, Marco; Preto, Nereo; Hinnov, Linda A.; Huang, Chunju; Rusciadelli, Giovanni, 2011; Terrestrial laser scanner imaging reveals astronomical forcing in the Early Cretaceous of the Tethys Realm, Earth and Planetary Science Letters, May 15, 2011, vol. 305, Issue 3-4, pp. 359-370.

Kurz, Tobias, Buckley, Simon, Schneider, Danilo, Howell, John, 2010, Ground-based hyperspectral imaging for the mapping of geological outcrop composition, Geophysical Research Abstracts, vol. 12, 2010.

Xu, X., 2000, Three-dimensional virtual geology; photorealistic outcrops, and their acquisition, visualization and analysis University of Texas at Dallas, Richardson, TX, United States, Doctoral thesis (2000) 170 pp.

Sabins, Floyd F., 2007, Remote Sensing, Principles and Interpretation Third Edition, Waveland Press, Inc. Long Grove, IL, p. 2-27; 177-210; 255-290 and 378-380.

Vincent, Robert K., 1997, Fundamentals of Geological and Environmental Remote Sensing, Prentice Hall, Upper Saddle River, NJ, p. 80-96.

Bellian, J.A., Beck, R.A., and Kerans, C., 2007 Analysis of hyperspecteral and lidar data: remote optical mineralogy and fracture identification : Geosphere, v. 3, No. 6, p. 491-500.

Agar, B., et al.; "Remote Sensing for Mineral Exploration—A Decade Perspective 1997-2007"; Paper 7, 2007, Plenary Session: The Leading Edge, pp. 109-136.

Kaasalainen, Sanna, et al.; "Toward Hyperspectral Lidar: Measurement of Spectral Backscatter Intensity With a Supercontinuum Laser Source"; IEEE Geoscience and Remote Sensing Letters, vol. 4, No. 2, Apr. 2007, pp. 211-215.

Weibring, P., et al.; "Multicomponent Chemical Analysis of Gas Mixtures Using a Continuously Tuneable Lidar System"; 2004, Applied Physics, vol. B79, pp. 525-530.

Wysocki, G et al.; "Widely Tunable Mode-Hop Free External Cavity Quantum Cascade Laser for High Resolution Spectroscopic Applications"; 2005, Applied Physics, vol. B81, pp. 769-777.

International Search Report, issued on Jun. 14, 2013, during the prosecution of International Application No. PCT/US2013/032330.

Written Opinion of the International Searching Authority, issued on Jun. 14, 2013, during the prosecution of International Application No. PCT/US2013/032330.

* cited by examiner

SYSTEM AND METHOD FOR INTERROGATION OF TARGET MATERIAL IN SITU

FIELD OF THE INVENTION

The present invention relates generally to a system and method for remotely sensing a target material in situ, and more particularly, a system and method for simultaneously providing ranging and hyperspectral data for the target material.

BACKGROUND OF THE INVENTION

Remote sensing of geometric shapes and locations of a target material has proven to be valuable in a number of fields, including for the study of geological formations. Conventional technologies include light detection and ranging ("lidar"), which is generally recognized as an "active" remote sensing technique that uses a single laser frequency to actively illuminate a target and determine range. Although a single frequency laser intensity value can offer some information about a target material's composition, identifying the chemical composition of the target material, such as specific mineralogy, cannot be accomplished by using a single frequency lidar instrument. A more complete spectral analysis of a target material requires multiple discrete frequencies to be simultaneously collected. Matching of separately obtained lidar information with hyperspectral data can require costly post-processing to perform resolution matching and illumination matching.

In addition, conventional spectral analysis techniques utilize spectral samples over multiple wavelengths of naturally occurring electromagnetic radiation, e.g., sunlight, to identify a target chemical composition. Such techniques are commonly referred to as "passive" remote sensing in that light is passively collected rather than actively directed at a target material. Spectral image analysis of passively collected data also requires considerable post-processing to extract meaningful results. Commercially available instruments cannot be dynamically modified during acquisition to collect maximum resolution of a target material based on real-time feedback from the instrument during acquisition.

Further, conventional spectral imaging techniques utilizing natural electromagnetic radiation are characterized by incomplete spectral coverage in the reflected infrared spectral region due to absorption of frequencies, e.g., 1400-1600 nm and 1800-2000 nm, from long transit distance through the atmosphere, e.g., several tens of kilometers. Using wide spectral bands, e.g., many tens of nanometers wide, is known to yield blurred spectral samples when inspecting the target material's spectral composition. Typically, many narrow bands are required, e.g., approximately 1 nm wide, to discretely determine chemical attributes of the target.

As such, a need exists to remotely sense target shape and target composition simultaneously across several hundred discrete wavelengths (~1 nm wide) while minimizing costly post-processing to perform resolution matching and illumination matching.

SUMMARY OF THE INVENTION

The device or apparatus described herein combines active hyperspectral imaging with simultaneous lidar measurements and integrates a materials database to allow for rapid adaptation of parameters, e.g., light frequency and spatial resolution of lidar, during acquisition based on real-time spectral feedback from the target material. The device or apparatus can pre-filter unwanted target areas and maximize spectral and spatial sampling of areas of high interest, thus reducing post-processing time and maximizing resolution in areas most desired.

Embodiments of the present invention generally include systems and methods for remotely sensing a target material in situ. The target material for example may be a embedded in outcrop located at a considerable distance from a system embodying the claimed invention.

In one embodiment, a system for remotely sensing a target material in situ includes a broad-band laser source, at least one tunable filter coupled to the source laser for generating a swept-frequency signal, and an optical device for splitting the swept-frequency signal into a first illumination signal and second illumination signal. The system further includes a first optical path for directing the first illumination signal unto the target material and receiving a reflected signal from the target material, a second optical path for receiving the second illumination signal and generating a spectral reference signal, and a control system coupled to the first optical path and the second optical path. The control system performs a comparison of the spectral reference signal and the reflected signal, and adjusts the frequency and spatial resolution of the laser source based at least in part on the comparison.

The system may also include a materials identity database for determining a chemical composition of the target material. In another embodiment, a method for remotely sensing a target material in situ includes illuminating the target material with a broadband swept frequency signal, illuminating a reference material representative of the target material with a portion of the broadband swept frequency signal to generate a reference spectrograph, receiving a first reflected signal from the target material, comparing the reference spectrograph to the first reflected signal to identify a frequency band of interest related to the target material, adjusting the broadband swept frequency signal based at least in part on the comparison of the reference spectrograph and the first reflected signal, and illuminating the target material with the adjusted broadband swept frequency signal to produce a second reflected signal having a higher spatial and spectral resolution within the frequency band of interest than that of the first reflected signal.

The method may also include the steps of receiving the second reflected signal from the target material, and comparing the second reflected signal via a materials database to determine a chemical composition of the target material within the frequency band of interest.

The ability to collect spectral data across many hundred to thousand discrete light frequencies at a single point, combined into a single coherent image offers an advantage over conventional imaging techniques, such as combing lidar and spectral images (conventional photographs, spectral scanners and/or imagers) in that spatial distortion from optical lenses is minimized and errors encountered by mis-registration of image-to-spatial model.

Additionally, the relatively short travel distance of the electromagnetic radiation from the source to detector in ground-based/terrestrial scanning lidar (ten cm-to-thousands of meters) allows a user to investigate frequency relationships attenuated by traditional, passive, hyperspectral imaging techniques that rely on sunlight traveling through the Earth's atmosphere.

This invention also uses both electro-optical tuning of laser output, mirror-deflection, and peizo-electric nano-deflection techniques to scan target sub-regions at ultra-high resolution as defined by attribute mapping in real time.

BRIEF DESCRIPTION OF THE DRAWINGS

A description of the present invention is made with reference to specific embodiments thereof as illustrated in the appended drawings. The drawings depict only typical embodiments of the invention and therefore are not to be considered limiting of its scope.

DETAILED DESCRIPTION OF THE INVENTION

Embodiments of the present invention for in situ interrogation of target materials are now described with reference to the appended drawings. The invention can be practiced as any one of or combination of hardware and software, including but not limited to a system (including a computer processor), a method (including a computer implemented method), an apparatus, an arrangement, a computer readable medium, a computer program product, a graphical user interface, a web portal, or a data structure tangibly fixed in a computer readable memory. An article of manufacture for use with a computer processor, such as a CD, pre-recorded disk or computer program storage medium having program code residing therein, also falls within the spirit and scope of the present invention.

Applications of the present invention include but are not limited to the acquisition of physical shape and chemical composition of target material from a remote location without the need for physical contact or disruption of the target material. Embodiments of the present invention may be applied in a number of different fields, including, hydrocarbon exploration and production, mining, civil engineering, general geological research, and any other field requiring non-destructive 3-D mapping of chemical and geometric attributes at variable scales of observation. Hydrocarbon exploration and production applications include but are not limited to outcrop analysis, downhole applications and subsea applications. Embodiments may include portable instruments, handheld devices or maneuverable downhole devices that simultaneously integrate active scanning of spectral and spatial information from a single broad-band light source that take measurements spectrally and spatially with the same laser source. The appended drawings illustrate only typical embodiments of the present invention and therefore are not to be considered limiting of its scope and breadth.

Figure 1:
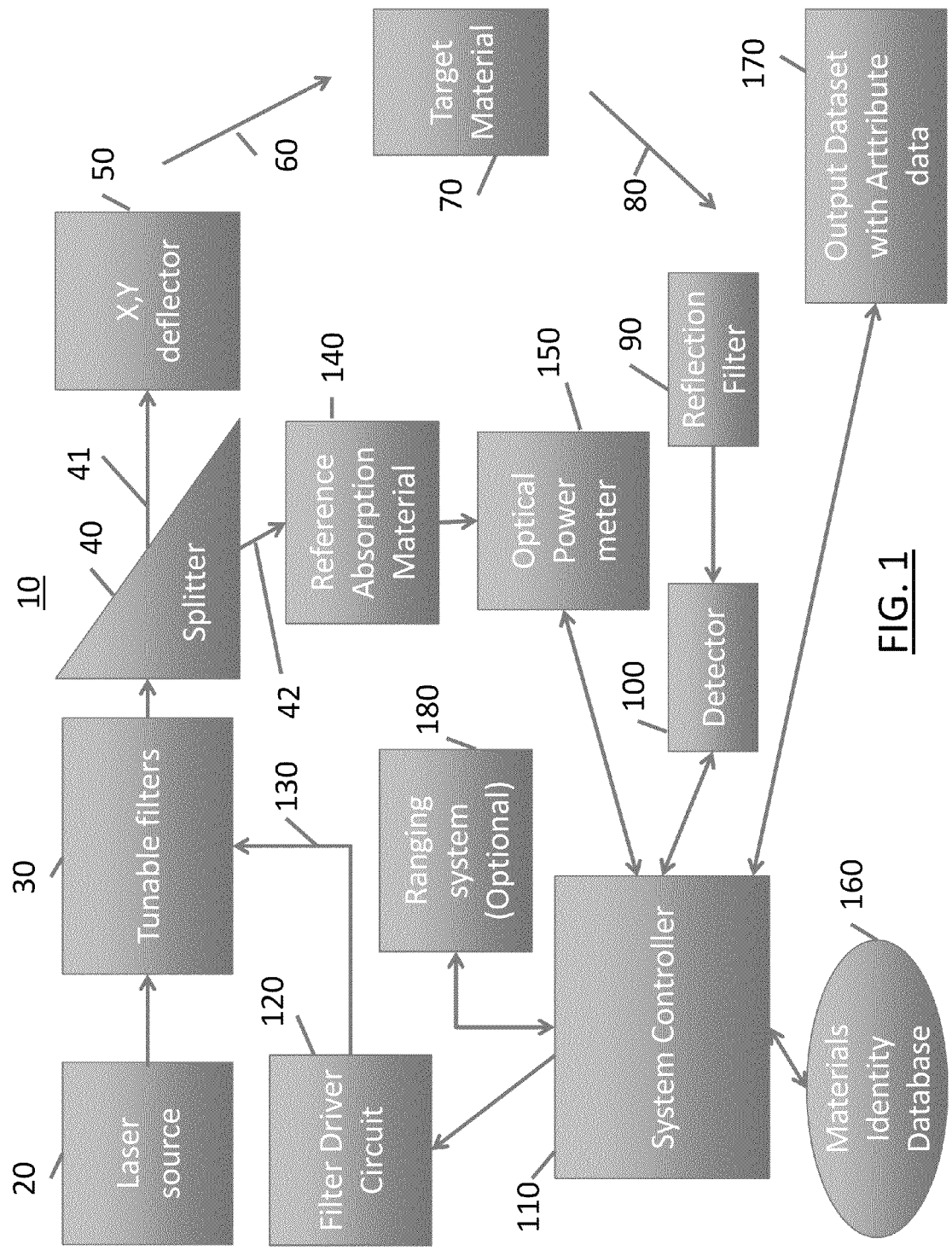
FIG. 1 is a block diagram of a system for active remote sensing in accordance with the present invention.

FIG. 1 shows an embodiment of an integrated system 10 that can be implemented as a field-portable system or apparatus and that is capable of simultaneously determining, remotely at a stand-off distance (e.g., 5 to 2,000 m or more) from a target material 70, the material's chemical composition, crystal/grain size and physical shape. The system 10 includes a swept-wavelength optical source having a light source 20 and a tunable filter 30 for producing optical radiation at a selectable frequency or frequencies within a frequency range of interest corresponding to a target material in situ. The swept-wavelength optical source may include diode, gas, solid or other types of tunable light sources. The emitted light may be characterized by a range of wavelengths suitable for active remote sensing including visible, ultra-violet and infrared.

In one embodiment, the light source 20 is a single frequency (<1 nm) broadband laser and the tunable filter 30 is a Fabry-Perot etalon filter 30 controlled by a system controller 110 to precisely adjust the frequency of the light close to the ideal Airy function (sub-nanometer resolution) and to ensure natural light is not obscuring data of interest. The combination of the broadband laser and Fabry-Perot etalon filter this uses broadband illumination for hyperspectral imaging, which does not rely on ambient light or natural conditions. can improve resolution by three or more orders of magnitude over previous art.

Referring again to FIG. 1, a first portion 41 of the output of the swept-wavelength optical source is directed via a targeting device 50, such as an X-Y deflector or beam direction device. The targeting device enables precise illumination via optical signal 60 of the target material 70 in situ in the X-Y plane within a scene (e.g., land, sea, atmosphere, etc.) at some distance from the swept-wavelength optical source. A portion of the optical signal 60 is reflected back 80 and detected via a receiver. The receiver may include any suitable combination of optical, opto-electronic, and/or electronic components 90 to filter and/or process light reflected from the target material 70, and detector electronics 100, including for example optical diodes, analog filters, analog-to-digital converter, etc., to convert the received optical signal 80 into an electrical signal that can be used by the system controller 110 to control the sweep of the swept-wavelength optical source and to determine the chemical composition of the target material via a materials identity database 160.

Figure 2:
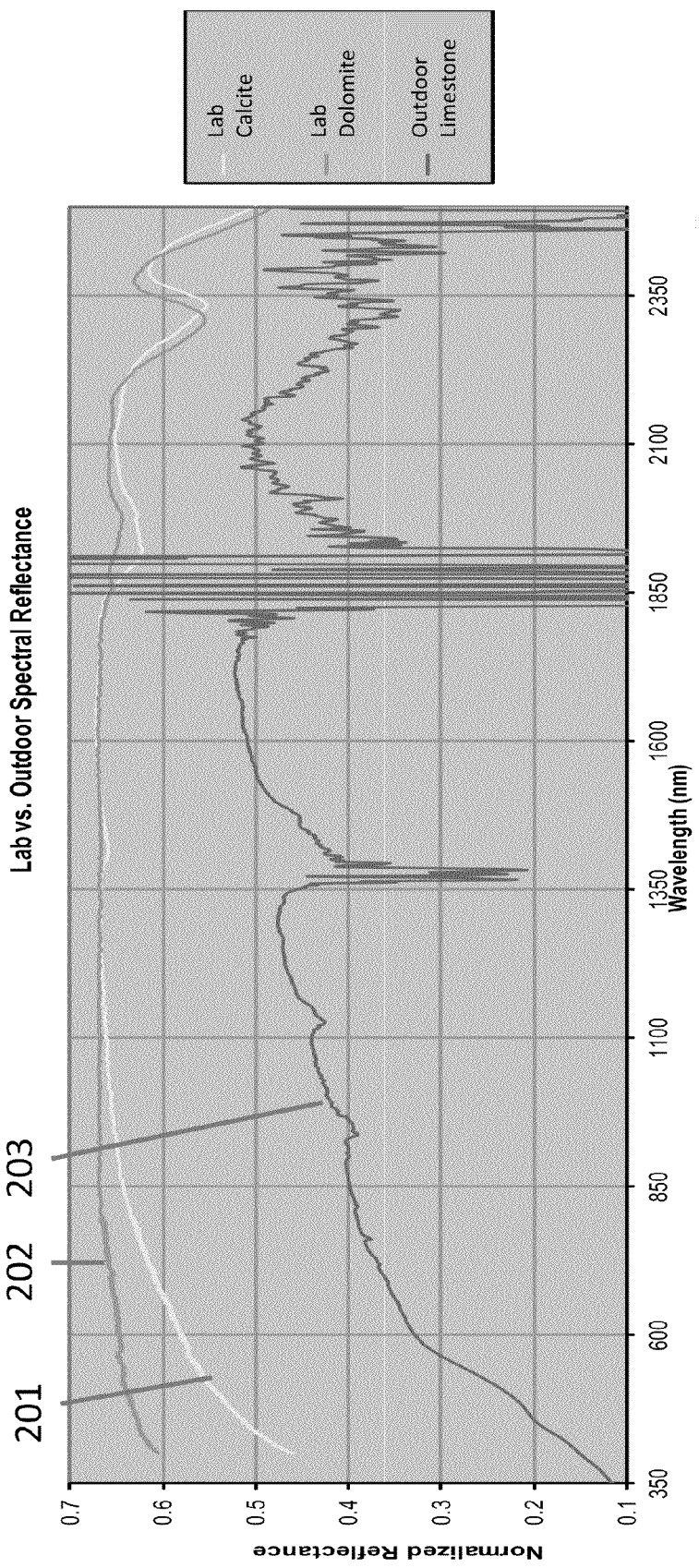
FIG. 2 is an exemplary reference spectrograph for a number of target materials in accordance with an aspect of the present invention.

Concurrently, a second portion 42 of the output of the swept-wavelength optical source is provided to a reference absorption material 140 to produce a spectral reference signal or spectrograph. See FIG. 2, for example, which shows reflectance data for two indoor pure mineral samples, calcite 201 and dolomite 202, and an outdoor limestone sample 203. The reference absorption material 140 may include a volume of solid and/or gaseous material found in the target material and which have similar absorption/reflection characteristics as the target material. The reference material generates a reference optical signal, which can be measured and used to generate a representative reference signal for use by the controller. By comparing the reference signal to electrical signal representative of the reflected signal from the target material, the controller can adjust the characteristics of the swept-wavelength optical signal. The controller thus adjusts the tunable filter so that the emitted light from the light source is the same frequency and shape of the spectral reference signal.

Optionally, an optical power meter 150 can be used for enhancing the spectral reference signal. In one embodiment, the output from power meter 150 is used by the system controller 110 to control the frequency sweep via the optical filter. For example, if a frequency range or band of interest corresponding the material is to be detected, the sweep can be controlled to improve the signal-to-noise ratio (SNR) to minimize the effects due to the variations in the reflected optical signal (from target material), and noise introduced via the laser source, receiver and other optical components in the system. The output signal of the power meter can also be used to more precisely control the interrogation time at the frequency range of interest. By more precisely controlling SNR and interrogation time, the accuracy of the measurement at detector 100 can be improved within the frequency range of interest.

As such, the system 10 auto-eliminates and filters out "obstructions" and focuses acquisition on desired or specified target composition at a desired spatial resolution, thus reducing post-processing and increasing efficiency by providing pre-processed images in real time.

Referring again to FIG. 1, the system controller 110 may be implemented using any suitable computer processor, such as an embedded controller, programmable logic controller or personal computer, programmed with computer readable program code or logic for controlling the sweep of the optical source and for determining the chemical composition of the target material. To control the sweep of the optical source, the system controller uses the electrical signals from the detector to control the tunable filter. Using computer program code embedded within the controller, the controller generates control signals to adjust one or more of the following via the tunable filter: frequency sweep range, sweep rate, and/or source optical output power.

In one embodiment, the operation of the Fabry-Perot etalon filter 30 is controllable by electronic signals generated by system controller 110 and which are tunable to various ranges and resolutions via filter driver circuit 120. The system controller 110 adjusts the intensity of source, sweep and time at frequency, etc., and increases SNR of the received signal by collecting more data at a desired frequency or frequency range. As such, the spectral and spatial resolution of the system 100 can be modified in response to environmental feedback from targets of interest and so as to eliminate undesirable spectral and spatial data.

Optionally, ultra-high spatial resolution can be achieved by modulating piezo-electric materials which deform when driven by a voltage signal. The driving waveform for such an arrangement of piezo-electrical materials can be used to "focus" and over sample on a specific target areas in the x-y dimension.

The system controller 110 is also arranged and configured to communicate with a materials identity database 160 to determine the chemical composition of the target material. Advantageously, the database 160 is used to create real-time image maps of spectral composition to drive spatial and spectral resolution of the system 10. The system controller 110 is configured to identify targets of interest by comparing incoming signals (from detector 100) to materials database 160. Each X-Y position and corresponding absorption measurement is used to assign an attribute value of spatial position and composition. The reference absorption material corresponds to the bandwidth of interest for the target material, e.g., calcite, dolomite, ankerite, etc., and helps identify any undesired attenuation or shift in frequency due to variable illumination, contamination, water content in atmosphere, etc. The compositional attribute values determined by comparison of incoming signal to the materials database 160 and user specified spatial or spectral attributes, and are used to focus the Fabry-Perot etalon 30 and detector filters 90. This feedback reduces post-processing requirements and makes it possible to gather additional spectral and spatial data in regions of interest in an automated manner.

The materials identity database 160 can therefore be used to modify acquisition parameters or create real-time attribute maps for in situ field inspection. In one embodiment, the materials database is a look-up table having frequencies $f_1$, $f_2$, $f_3 \ldots f_n$ and corresponding optical intensity information $I_1$, $I_2$, $I_3 \ldots I_n$ for one or more target materials of interest. The real-time attribute maps with input from the materials database 160 offers the user the ability to specify high-grade acquisition parameters and seek out desired patterns such as specific elemental metal content or proportions of specific elements within the entire or a subset of the target area. An example of this type of application would be to determine Mg and/or Fe content within a sample pixel of the mineral dolomite (the proportion of which alter the crystalline matrix and thus the spectral reflectance signature).

In accordance with one embodiment of the present invention, an interface is arranged and configured to interact with the materials identity database 160. The interface can be used in real-time to identify materials within the scan area containing chemical composition on the basis of spectral response compared to materials database to activate ultra-high resolution.

In another embodiment, the interface overlays a color-coded map identifying mineral content of interest generated on the basis of minerals database matching and identification and shows a key legend that decodes and associates the color coding to a mineral content identification. The user can then interact with the interface using any of several known established user interface techniques like a mouse or touch screen to indicate one or more mineral compounds of interest selected from the key legend on the interface. In response to the identification of one or more mineral compounds of interest, the system in accordance with the present invention adjusts the resolution of discrete frequencies acquired, and performs an acquisition in two-dimensional areas that contain minerals compounds identified as chemical compositions of interest. Hyperspectral frequency acquisition adjustment can be accomplished, for example, dynamically by using a regulated adjustment of an electrical control signal sent to a piezo-electric based filter element which translates the electrical signal to physical movement and thus controls filtering. By adjusting the electrical control signal, the invention may limit the action of the filters to a subset of frequencies associated with the mineral composition of interest identified by the user. Hyperspectral frequency resolution acquisition can be increased and decreased by orthogonally adjusting the electrical control signal sweep frequency allowing for sufficient acquisition of the light detector 100. Increasing the electrical control signal sweep time decreases the amount of time the emitted light band stays at a single frequency and therefore reduces the time available for the light detector 100 to sense the light intensity. Decreasing the electrical control signal sweep time has the opposite effect allowing for longer light detector sensing times and multiple intensity measurements. Multiple intensity measurements are used in an averaging scheme to increase the accuracy of the measurement and can even help eliminate spurious anomaly measurements caused by interfering transient reflections.

In summary, implementation of materials database 160 allows for the control of a swept-frequency optical source based on real-time feedback from the spectral signature of the target material. Compositional attribute clusters are identified during the scanning at normal resolution (e.g., 1-50 cm sample), and the user can be requested to identify which attribute clusters require additional sampling for ultra-high resolution (e.g., sub-millimeter) spectroscopic chemical analysis.

Applications of the present invention cover many disciplines including sample identification in laboratories to long-range field analysis at distances from the target material. The range from which a sample may be identified is governed by the power of the light source to retain a high SNR over longer transit time. In the field of geological science, for example, geological mapping may be greatly enhanced by the ability to quantitatively, precisely and accurately measure both shape and composition of an exposed rock surface simultaneously. This is especially true when frequencies outside the visible spectrum are captured that the human eye cannot detect. Information in the reflected infrared spectral range (e.g., ~800-2500 nm) has been proven to contain diagnostic reflectance and absorption characteristics for geological samples. Conventional passive hyperspectral imaging is limited not only to the quality of natural light during image acquisition but also attenuation of frequencies (e.g., 1400-1600 nm and 1800-2000 nm) as light from the Sun is filtered by Earth's atmosphere. Advantageously, a system in accordance with the present invention can more effectively detect reflections across the entire visible and reflected infrared spectral range due to the relatively short time of flight (e.g., less than 10 km) of the sweep-frequency laser and provide thus more robust spectral composition identification of target material.

In accordance with another embodiment of present invention, the system 10 can be combined with an optional ranging system 180, such as a passive imaging device or external lidar device, to also obtain range information to the target material. The combination of hyperspectral imaging with source illumination and a single-frequency lidar provides an active remote sensing device that can be used to simultaneously range and identify composition and shape of the target material in variable lighting to complete darkness.

Figure 3:
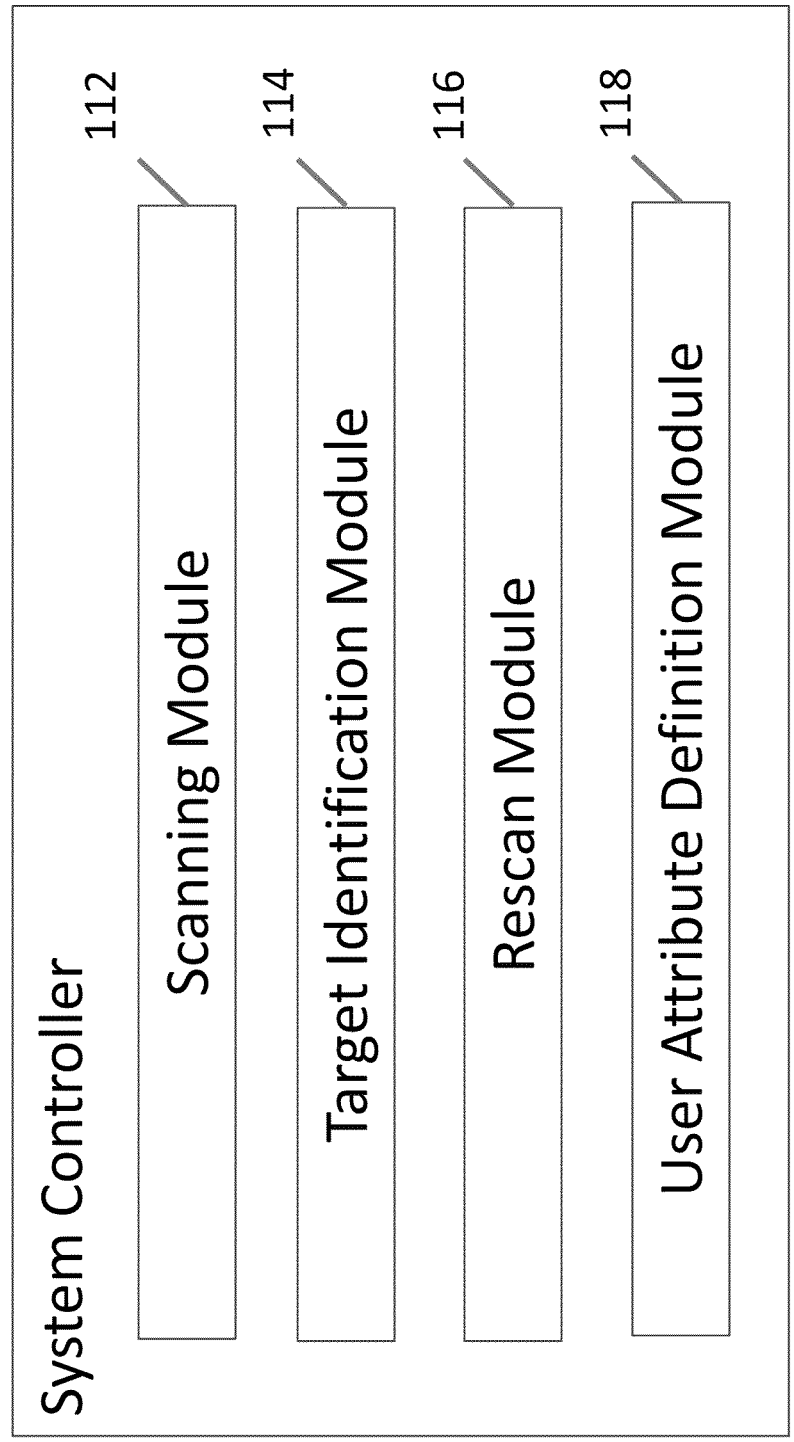
FIG. 3 is a block diagram of an exemplary system controller for the active remote sensing of FIG. 1.

FIG. 3 is a block diagram of the system controller 110 in accordance with an embodiment of the present invention. System controller includes scanning module 112, target identification module 114, rescan module 116, and user attribute definition module 118. Scanning module 112 is used to control a first overall scan of the target material. In accordance with an embodiment of the present invention, the scanning module 112 controls an output of the light source, including its light frequency emitted and dwell time at each frequency. Target identification module 114, is used to identify targets of interest and to add desired attributes to saved data from overall scan resulting from the scanning module 112. Module 114 interfaces with the materials database to identify a material based on its spectral reflectance values for a given frequency or set of frequencies. Rescan module 116 is used to rescan areas of interest with higher spectral and spatial data to create attribute maps of spatial position and composition. Module 116, for example, controls the nano-scan "ultra-high resolution piezo-electric apparatus" triggering when a specific target material is identified by the target identification module 114.

User attribute definition module 118 allows a user to define attributes of interest. Module 118 allows the user to select an area of the image of known interest-but-possibly not known chemical composition and "flag" it with an attribute (rock type A) and all points that fall within that region (spatial or spectral region) can be labeled with "rock type A"; this may help identify mixed signals in the field if a target material is partially covered by vegetation or other debris. The purpose is to help the user guide the instrument if he or she knows a particular area is critical to collect specific frequency data from. The user attribute definition module 118 may include computer readable code for generating one or more interfaces as described above for real-time identification of materials within a scan area. In response to the identification of one or more mineral compounds of interest, the interfaces can be used by the user to adjust the resolution of discrete frequencies acquired, and to control the acquisition in two-dimensional areas that contain minerals compounds identified as chemical compositions of interest.

In addition to the embodiments of the present invention described above, further embodiments of the invention may be devised without departing from the basic scope thereof. For example, it is to be understood that the present invention contemplates that one or more elements of any embodiment can be combined with one or more elements of another embodiment. It is therefore intended that the embodiments described above be considered illustrative and not limiting, and that the appended claims be interpreted to include all embodiments, applications and modifications as fall within the true spirit and scope of the invention.

What is claimed is:

1. A system for remotely sensing a target material in situ, comprising:
   a broad-band laser source; at least one tunable filter coupled to the source laser for generating a swept-frequency signal;
   an optical device for splitting the swept-frequency signal into a first illumination signal and second illumination signal;
   a first optical path for directing the first illumination signal unto the target material and receiving a reflected signal from the target material;
   a second optical path for receiving the second illumination signal and generating a spectral reference signal; and
   a control system coupled to the first optical path and the second optical path for adjusting the frequency and spatial resolution of the laser source based at least in part on a comparison of the spectral reference signal and the reflected signal.

2. The system according to claim 1, wherein the first optical path comprises a deflector.

3. The system according to claim 1, wherein the first optical path comprises a reflector filter.

4. The system according to claim 1, wherein the first optical path comprises a light detector.

5. The system according to claim 1, wherein the second optical path comprises a reference absorption material.

6. The system according to claim 1, wherein the second optical path comprises an optical power meter.

7. The system according to claim 1, wherein the control system comprises a system controller.

8. The system according to claim 7, wherein the controller comprises a computer processor programmed with computer readable media program, and wherein the computer readable media program comprises: a scanning module for controlling a scan of the target material; a target identification module for identifying targets of interest for adding desired attributes to data resulting from the scan; and a rescan module for rescanning areas of interest relate to the target material with higher spectral and spatial data to create attribute maps spatial position and composition.

9. The system according to claim 8, wherein the computer readable media program further comprises a user attribute definition module for defining spatial position and composition attributes of interest.

10. The system according to claim 1, wherein the control system comprises a materials identity database for determining a chemical composition of the target material.

11. The system according to claim 1, wherein the control system comprises a filter driver circuit.

12. The system according to claim 1, further comprising a light detection and ranging subsystem for simultaneously determining range information related to the target material.

13. A method for remotely interrogating a target material in situ, comprising:
   illuminating the target material with a broadband swept frequency signal; illuminating a reference material representative of the target material with a portion of the broadband swept frequency signal to generate a reference spectrograph;
   receiving a first reflected signal from the target material; comparing the reference spectrograph to the first reflected signal to identify a frequency band of interest related to the target material;

adjusting the broadband swept frequency signal based at least in part on the comparison of the reference spectrograph and the first reflected signal; and illuminating the target material with the adjusted broadband swept frequency signal to produce a second reflected signal having a higher spatial and spectral resolution within the frequency band of interest than that of the first reflected signal.

14. The method according to claim 11, further comprising: receiving the second reflected signal from the target material; and comparing the second reflected signal via a materials database to determine a chemical composition of the target material within the frequency band of interest.

15. The method according to claim 11, further comprising simultaneously determining range information related to the target material.

16. An article of manufacture comprising a non-transitory, computer readable medium having a computer readable code embodied therein, the computer readable code being adapted to execute a method for remotely interrogating a target material in situ, the method comprising:

illuminating the target material with a broadband swept frequency signal; illuminating a reference material representative of the target material with a portion of the broadband swept frequency signal to generate a reference spectrograph;

receiving a first reflected signal from the target material; comparing the reference spectrograph to the first reflected signal to identify a frequency band of interest related to the target material;

adjusting the broadband swept frequency signal based at least in part on the comparison of the reference spectrograph and the first reflected signal; and illuminating the target material with the adjusted broadband swept frequency signal to produce a second reflected signal having a higher spatial and spectral resolution within the frequency band of interest than that of the first reflected signal.

17. The article of manufacture according to claim 16, wherein the method executed by the computer readable code further comprises the step of simultaneously determining range information related to the target material.

* * * * *